United States Patent [19]

Kim

[11] Patent Number: 4,496,540
[45] Date of Patent: Jan. 29, 1985

[54] THERAPEUTIC COMPOUNDS
[75] Inventor: Sun K. Kim, Chestnut Hill, Mass.
[73] Assignee: Biomeasure, Inc., Hopkinton, Mass.
[21] Appl. No.: 454,731
[22] Filed: Dec. 30, 1982
[51] Int. Cl.³ ............... C07C 103/52; A61K 37/02
[52] U.S. Cl. .................. 514/19; 260/112.5 R; 514/867; 514/809
[58] Field of Search .............. 424/177; 260/112.5 R
[56] References Cited

U.S. PATENT DOCUMENTS 4,146,644 3/1979 Griffith et al. ............... 424/320

FOREIGN PATENT DOCUMENTS 8008601 10/1981 France.

OTHER PUBLICATIONS

Llorens et al., (1981) Eur. J. Pharm. 69 113–116.
Roques et al., (1980) Nature 288 286–288.
Coletti-Prieviero et al., (1982) B.B.R.C. 107 465–469.
Schwartz et al., (1981) Life Sciences 29 1715–1740.
Llorens et al., (1980) B.B.R.C. 96 1710–1716.
Blumberg et al., (1981) Life Sci. 28 301–306.
Hachisu et al., (1982) Life Sci. 30 1739–1746.
Algieri et al., (1981) Eur. J. Pharm. 74 261–262.
Bodner et al., (1980) Pharm. Blochem. Behav. 13 829–833.
Hudgin et al., (1981) Life Sci. 29 2593–2601.

Primary Examiner—Delbert R. Phillips
Assistant Examiner—F. T. Moezie

[57] ABSTRACT

In one aspect, compounds capable of inhibiting an endopeptidase responsible for a degradation pathway of enkephalin and having the general formula

A—B—NHOH wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine; or a pharmaceutically acceptable salt thereof.

20 Claims, No Drawings

THERAPEUTIC COMPOUNDS

BACKGROUND OF THE INVENTION

This invention relates to amino acid-containing therapeutic compounds.

The endogenous analgesic oligopeptides known as the enkephalins are known to be cleaved by an endopeptidase referred to as enkephalinase. Enkephalinase is known to be inhibited by a number of substances, including "the dipeptide Phe-Ala and the thiol derivative Thiorphan"; Llorens et al. (1981) Eur. J. Pharm. 69, 113. Thiorphan ((DL-3-mercapto-2-benzylpropanoyl) glycine), described in U.S. Pat. No. 3,008,601, "protects the enkephalins from the action of enkephalinase in vitro in nanomolar concentration and in vivo after either intracerebroventricular or systemic administration"; Roques et al. (1980) Nature 288, 5788. It was reported in Coletti-Prieviero et al. (1982) B.B.R.C. 107, 465 that amino acid hydroxamates containing, respectively, tryptophan, tyrosine, phenylalamine, arginine, and alanine inhibited enkephalin in vitro. The presence of both enkephalinase and enkephalin receptors has been demonstrated in many tissues in addition to the brain. For example, enkephalin receptors have been found in dog intestine; Oka, TIPS (1981), and enkephalinases have been found in salivary glands, thyroid tissue, lung, kidney, and adrenal tissue. A low level of enkephalins, in addition to being associated with hyperalgesia, has been implicated in mental depression; Emrich in *Typical and Atypical Antidepressants: Clinical Practice,* Costa et al., eds. (1982).

SUMMARY OF THE INVENTION

In general, the invention features, in one aspect, compounds capable of inhibiting an endopeptidase responsible for a degradation pathway of enkephalin and having the general formula $$A—B—NHOH \quad (1)$$

wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine; or a pharmaceutically acceptable salt thereof.

Preferred compounds within Formula (1) are L-tyrosyl-D-alanine hydroxamate, L-tyrosyl-L-alanine hydroxamate, L-phenylalanyl-D-alanine hydroxamate, L-phenylalanyl-L-alanine hydroxamate, and L-phenylalanyl-L-leucine hydroxamate.

In another aspect, the invention features compounds capable of inhibiting an endopeptidase responsible for a degradation pathway of enkephalin and having the formula $$Z—A—B—NHOH \quad (2)$$

wherein A and B are as defined above for Formula (1) and Z is a protecting group for amino acid residue A.

Preferred compounds within Formula (2) are benzyloxy carbonyl ("CBZ")-L-tyrosyl-L-alanine hydroxamate, CBZ-L-tyrosyl-D-alanine hydroxamate, CBZ-L-phenylalanyl-D-alanine hydroxamate, CBZ-L-phenylalanyl-L-alanine hydroxamate, and CBZ-L-phenylalanyl-L-leucine hydroxamate.

In other preferred embodiments, a therapeutically effective amount of the therapeutic compound and a pharmaceutically acceptable carrier substance, e.g. magnesium carbonate or lactose, together form a therapeutic composition, e.g. a pill, tablet, capsule, or liquid for oral administration to a human patient, a spreadable cream, gel, lotion, or ointment for application to the skin of a human patient in need of the compound for the relief of pain, itching, or irritation, or a liquid capable of being administered nasally as drops or spray. The pill, tablet, or capsule can be coated with a substance capable of protecting the composition from the gastric acid in the patient's stomach for a period of time sufficient to allow the composition to pass undisintegrated into the patient's small intestine.

The compounds of the invention are active in inhibiting an endopeptidase responsible for a degradation pathway of enkephalin, rendering the compounds useful in a variety of therapeutic applications. Furthermore, their low molecular weight facilitates administration and absorption.

Other features and advantages of the invention will be apparent from the following description of the preferred embodiments thereof, and from the claims.

DESCRIPTION OF THE PREFERRED EMBODIMENTS

We turn now to a description of preferred embodiments of the invention.

STRUCTURE

The compounds of the invention have the general formula recited in the Summary of the Invention above. Examples of preferred compounds within the general formula are those referred to as preferred embodiments above.

The compounds are dipeptide hydroxamates (protected or unprotected) in which a hydroxyamino group is attached to the C-terminal amino acid via an amido linkage, and in which the N-terminal amino acid is an aromatic group-containing amino acid.

The compounds can be provided in the form of pharmaceutically acceptable salts, e.g. salts made with potassium hydroxide, sodium hydroxide, or dicyclohexylamine.

SYNTHESIS

The compounds can be prepared by reacting an appropriately protected amino acid of the formula

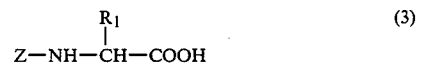

where Z is an amino acid protecting group such as benzyloxycarbonyl, p-methoxybenzyloxy carbonyl, p-nitrobenzyloxycarbonyl, p-chlorobenzyloxycarbonyl, trifluoroacetyl, or benzyl, and $R_1$ is the identifying group of L- or D-phenylalanine, L- or D-tyrosine, or L- or D-tryptophan, with an amino acid ester of the formula

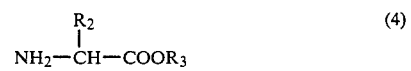

where $R_2$ is the identifying group of L- or D-alanine, L- or D-leucine, L- or D-isoleucine, or glycine, and $R_3$ is a carboxyl group protecting group such as lower (fewer than 6 carbon atoms) alkyl, benzyl, or phenyl, to form a protected dipeptide ester of the formula

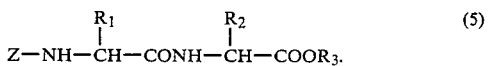

Amino acid esters are commercially available or can be prepared by conventional methods, e.g. that described in Greenstein et al., Chemistry of the Amino Acid, Vol. 1–3 (1961). The reactions are expediently carried out in an inert organic solvent, preferably a polar organic solvent such as dimethylformamide, tetrahydrofuran, acetonitrile, or a halogenated hydrocarbon such as dichloromethane, and are carried out at temperatures below room temperature in order to minimize side reactions. The reactions can be conducted by employing conventional condensation techniques for the formation of peptide bonds. A wide range of protecting and activating groups as well as condensation procedures are described in Schroeder et al., The Peptides, Vol. 1–2 (1965, 1966) and Gross et al., The Peptides, Vol. 1–3 (1979, 1980, 1981).

The protected dipeptide ester is then reacted with a large excess of hydroxylamine to yield a protected dipeptide hydroxamate of the formula

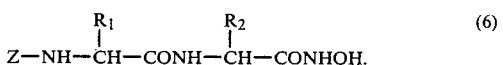

The protecting group, Z, is either left to form part of the final product or, if desired, is removed by catalytic hydrogenation using palladium on charcoal as the catalyst in the presence of a suitable solvent, e.g. water or alcohol.

The intermediates and final product can be isolated and purified by column chromatography or crystallization. Purity can be determined using chromatographic, spectroscopic, and analytic techniques.

Specific compounds were made as follows.

CBZ-L-Tyrosyl-D-Alanine hydroxamate

The first intermediate, D-alanine methylester hydrochloride, was prepared as follows. 2 gm D-alanine was suspended in 200 ml methanol and dry hydrogen chloride gas was passed through the suspension until a clear solution formed. The solution was cooled in an ice bath while saturated with dry hydrogen chloride. The reaction mixture was kept at room temperature overnight. Solvent and excess hydrogen chloride was removed in vacuo and the residual hydrogen chloride was removed by repeated co-evaporation with methanol. The residue was triturated with ether to afford 3.07 gm of solid.

The nest intermediate, benzyloxycarbonyl-L-tyrosyl-D-alaninemethylester, was prepared by cooling a solution of 0.5 gm D-alanine methylester hydrochloride in 5 ml tetrahydrofuran to 0° C. and treating with 0.48 ml N-methylmorpholine. After stirring 15 min., 1.13 gm benzoloxycarbonyl-L-tyrosine, and 0.879 gm 1-hydroxybenzotriazole were added to the solution. A cold solution of 0.82 gm dicyclohexylcarbodiimide in 2 ml tetrahydrofuran was added and the mixture was stirred at 0° C. for 1 hr and then at room temperature overnight. After addition of 0.2 ml glacial acetic acid the mixture was stirred for 5 min., filtered, and the filtrate was concentrated in vacuo to dryness. The residue was redissolved in 50 ml ethylacetate, washed with water, 1N HCl, water, 10% aq. NaHCO$_3$, and water, and was then dried using MgSO$_4$. The solvent was removed in vacuo, and the residue was subjected to silica gel column chromatography (silica 40 gm) using CHCl$_3$ followed by CHCl$_3$-acetone (9:1) as eluant. Appropriate fractions were pooled and solvent removed in vacuo to afford 630 mg of white solid having a melting point of 161°–162° C. TLC on silica gel using an eluent of 3 CHCl$_3$:1 acetone gave Rf=0.33.

Benzyloxycarbonyl-L-tyrosyl-D-alanine hydroxamate was prepared by treating a solution of 0.3 gm hydroxylamine hydrochloride in 8 ml methanol with 5 ml 1N NaOCH$_3$. After standing for 5 min., the supernatant was decanted from the formed NaCl, and was reacted with 0.2 gm benzyloxycarbonyl-L-tyrosyl-D-alanine methylester. After overnight stirring, additional hydroxylamine was added and stirring continued another 24 hr. Solvent was removed in vacuo to dryness and the residue was tritirated with water to remove excess hydroxylamine, then dried. The crude product was chromatographed on silica gel (15 gm) using chloroform-methanol (9:1) as eluant. Appropriate fractions were pooled and the solvent was removed in vacuo to afford 0.12 gm of light tan solid. TLC on silica gel using an eluent of 3 CHCl$_3$:1 MEOH gave Rf=0.56. IR spectroscopy of the intermediate in a KBr pellet showed an absence of 1750 cm$^{-1}$ (ester). FeCl$_3$ analysis was positive (brown, hydroxylamino).

L-tyrosyl-D-Alanine hydroxamate

An aqueous slurry of 90 mg 10% Pd-C was added to a solution of 400 mg benzyloxycarbonyl-L-tyrosyl-D-alanine hydroxamate in 4 ml methanol. Hydrogenation was carried out under 1 atmosphere overnight. The mixture was filtered through a celite pad and washed with methanol followed by water. After removal of solvents, 160 mg of pale yellow solid product was obtained. TLC on silica gel using an eluent of 3 CHCl$_3$:1 MEOH gave Rf=0.19.

Benzyloxycarbonyl-L-Phenylalanyl-D-Alanine Hydroxamate

First benzyloxycarbonyl-L-phenylalanyl-D-alanine methyl ester was prepared, as follows. A solution of 0.56 g of D-alanine methyl ester hydrochloride in 6 ml tetrahydrofuran was cooled to 0° C. and then treated with 0.53 ml of N-methylmorpholine. After 15 min of stirring, 1.20 g of benzyloxycarbonyl-L-phenylalanine and 1.08 g of 1-hydroxybenzotriazole were added. A cold solution of 0.99 g of N, N'-dicyclohexylcarbodiimide in 2 ml tetrahydrofuran was then added and the mixture stirred for 1 hour at 0° C., then overnight at room temperature. After adding 0.3 ml of glacial acetic acid, the mixture was stirred 5 min., filtered, and the filtrate concentrated in vacuo to dryness. The residue was dissolved in CHCl$_3$, washed 3 times with 5% aqueous NaHCO$_3$, dried over anhydrous Na$_2$SO$_4$, and the solvent removed in vacuo. The residue was purified by silica gel column chromatography (silica 60 g) using CHCl$_3$ followed by CHCl$_3$-acetone 10:1 as eluant. Appropriate fractions were pooled and the solvent removed in vacuo to obtain 0.74 g of white solid, m.p. 134–136 C. TLC on silica gel using an eluant of 10 acetone gave R$_f$=0.37.

A solution of 1.39 g of hydroxylamine hydrochloride in 5 ml of methanol was treated with 20 ml of 1N NaOCH$_2$. After 5 min. of standing, the supernatant was decanted from the precipitated NaCl and added to a solution of 0.71 g benzyloxycarbonyl-L-phenylalanyl-D-alanine methyl ester in 5 ml of methanol. After stirring overnight at room temperature, the pH was adjusted to 7 with 1N HCl, and the solvent was removed in vacuo. The residue was triturated with water to remove excess hydroxylamine, then dried to obtain 0.45 g of white solid, m.p. 147–179 C. TLC on silica gel using an eluant of 9 $CHCl_3$:1 methanol gave Rf=0.43. $FeCl_3$ analysis was positive (brown, hydroxylamino).

L-Phenylalanyl-D-Alanine Hydroxamate 0.27 g of benzyloxycarbonyl-L-phenylalanyl-D-alanine hydroxamate was dissolved in 10 ml methanol and 60 mg of 10% Pd/C was added in an aqueous slurry. Hydrogenation was carried out overnight under 40 psi hydrogen. The mixture was filtered through a celite pad and washed with methanol and then water. The filtrate was reduced to dryness in vacuo to obtain 0.17 g of pale yellow solid. TLC on silica gel using an eluant of 3 $CHCl_3$:1 Methanol:0.5 triethylamine gave Rf=0.32.

The following additional specific compounds were made using procedures analogous to those described above: CBZ-L-phenylalanyl-L-alanine hydroxamate; L-phenylalanyl-L-alanine hydroxamate; CBZ-L-phenylalanyl-L-leucine hydroxamate; L-phenylalanyl-L-leucine hydroxamate; CBZ-L-tyrosyl-L-alanine hydroxamate; and L-tyrosyl-L-alanine hydroxamate.

Use

When administered to mammals (e.g. orally, topically, intravenously, parenterally, nasally, or by suppository), the compounds can have central and peripheral chronic and acute analgesic effects. In addition, the compounds can have antidiarrheic and antidepressant actions, and can relieve the symptoms of respiratory distress. When used to relieve pain, the compounds can potentiate the analgesic activity of other analgesics (e.g., morphine) by inhibiting the endogenous metabolic degradation of enkephalins.

The compounds can be administered to a mammal, e.g. a human, in a dosage of 1.0 to 250 mcg/kg/day, preferably 5 to 100 mcg/kg/day.

Other embodiments are within the following claims.

I claim:

1. A compound capable of inhibiting an endopeptidase responsible for a degradation pathway of enkephalin and having the general formula A—B—NHOH
   wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine;
   or a pharmaceutically acceptable salt thereof.
2. A compound capable of inhibiting an endopeptidase responsible for a degradation pathway of enkephalin and having the general formula Z—A—B—NHOH
   wherein A is one of the aromatic group-containing amino acid residues L-tryptophyl, D-tryptophyl, L-tyrosyl, D-tyrosyl, L-phenylalanyl, or D-phenylalanyl, B is one of the amino acids glycine, L-alanine, D-alanine, L-leucine, D-leucine, L-isoleucine, or D-isoleucine, and Z is a protective group for amino acid residue A;
   or a pharmaceutically acceptable salt thereof.
3. The compound of claim 1, having the formula L-tyrosyl-D-alanine hydroxamate.
4. The compound of claim 1, having the formula L-tryosyl-L-alanine hydroxamate.
5. The compound of claim 1, having the formula L-phenylalanyl-D-alanine hydroxamate.
6. The compound of claim 1, having the formula L-phenylalanyl-L-alanine hydroxamate.
7. The compound of claim 1, having the formula L-phenylalanyl-L-leucine hydroxamate.
8. The compound of claim 2, having the formula CBZ-L-tyrosyl-L-alanine hydroxamate.
9. The compound of claim 2, having the formula CBZ-L-tyrosyl-D-alanine hydroxamate.
10. The compound of claim 2, having the formula CBZ-L-phenylalanyl-D-alanine hydroxamate.
11. The compound of claim 2, having the formula CBZ-L-phenylalanyl-L-alanine hydroxamate.
12. The compound of claim 2, having the formula CBZ-L-phenylalanyl-L-leucine hydroxamate.
13. A therapeutic composition for inhibiting an endopeptidase responsible for a degradation pathway of enkephalin comprising a therapeutically effective amount of the compound of claim 1 or claim 2 together with a pharmaceutically acceptable carrier substance.
14. The therapeutic composition of claim 13 wherein said composition is in the form of a pill, tablet, or capsule or oral administration to a human patient in need of said compound.
15. The therapeutic composition of claim 13 wherein said composition is in the form of a liquid for oral administration to a human patient in need of said compound.
16. The therapeutic composition of claim 14, said composition being coated with a substance capable of protecting said composition from the gastric acid in the stomach of said human patient for a period of time sufficient to allow said composition to pass undisintegrated into the small intestine of said human patient.
17. The therapeutic composition of claim 13, said composition being in the form of a cream, gel, spray, or ointment for application to the skin of a human patient in need of said compound for the relief of pain, itching, or irritation.
18. The therapeutic composition of claim 13, said composition being in the form of a liquid capable of being administered to said human patient nasally as drops or spray.
19. The compound of claim 1, wherein A or B is a D-amino acid residue as set forth in claim 1.
20. A method of treating a mammal in need of relief of pain comprising administering to said mammal a therapeutically effective amount of the compound of claim 1 or claim 2.

* * * * *